(12) United States Patent
Lincoln et al.

(10) Patent No.: US 11,963,891 B2
(45) Date of Patent: *Apr. 23, 2024

(54) PROSTHETIC JOINT WITH A MECHANICAL RESPONSE SYSTEM TO POSITION AND RATE OF CHANGE

(71) Applicant: OTTOBOCK SE & CO. KGAA, Duderstadt (DE)

(72) Inventors: Lucas Samuel Lincoln, Edmonds, WA (US); Ben Gilbert Macomber, Shoreline, WA (US); Nicholas Roy Corson, Mukilteo, WA (US); David Alan Boone, Seattle, WA (US)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 245 days.

This patent is subject to a terminal disclaimer.

(21) Appl. No.: 17/246,415

(22) Filed: Apr. 30, 2021

(65) Prior Publication Data

US 2022/0054284 A1 Feb. 24, 2022

Related U.S. Application Data

(62) Division of application No. 15/536,240, filed as application No. PCT/US2015/066614 on Dec. 18, 2015, now Pat. No. 11,013,622.

(Continued)

(51) Int. Cl.
*A61F 2/66* (2006.01)
*A61F 2/74* (2006.01)
(Continued)

(52) U.S. Cl.
CPC .... *A61F 2/6607* (2013.01); *A61F 2002/5006* (2013.01); *A61F 2002/5033* (2013.01);
(Continued)

(58) Field of Classification Search
CPC ............ A61F 2/6607; A61F 2002/5006; A61F 2002/5033; A61F 2002/5035;
(Continued)

(56) References Cited

U.S. PATENT DOCUMENTS 2,638,605 A 5/1953 Johnson
2,671,224 A * 3/1954 Regnell ................... A61F 2/604
623/44

(Continued)

FOREIGN PATENT DOCUMENTS

CN 2614648 Y 5/2004
CN 2614650 Y 5/2004
(Continued)

OTHER PUBLICATIONS

PCT International Search Report for corresponding PCT International Patent Application No. PCT/US2015/066614, dated Jun. 3, 2016.

(Continued)

*Primary Examiner* — Christie Bahena
(74) *Attorney, Agent, or Firm* — HOLLAND & HART LLP

(57) ABSTRACT

A prosthetic joint and a method of controlling dorsiflexion and plantarflexion of the hydraulic prosthetic ankle joint. The method includes generating ground reaction forces with a hydraulic prosthetic ankle, wherein the prosthetic hydraulic ankle comprises a first chamber and a second chamber, and the ankle is connected to a prosthetic foot; rotating the prosthetic foot in response to the ground reaction force; transferring fluid between the forward and rear chambers in response to rotation of the foot; providing a feature to occlude or partially occlude the fluid transfer between chambers; providing a non-electronic mechanism for controlling the flow responsive to both a position of the joint and (Continued)

a rate of change of position of the joint, and wherein the mechanism is arranged such that a dwell at a particular joint location or locations will occlude the flow path.

19 Claims, 24 Drawing Sheets

Related U.S. Application Data

(60) Provisional application No. 62/094,009, filed on Dec. 18, 2014.

(51) Int. Cl.
*F16F 9/48* (2006.01)
*F16F 9/512* (2006.01)
*A61F 2/50* (2006.01)
*A61F 2/68* (2006.01)

(52) U.S. Cl.
CPC .............. *A61F 2002/5035* (2013.01); *A61F 2002/5072* (2013.01); *A61F 2002/6818* (2013.01); *A61F 2002/6863* (2013.01); *A61F 2/74* (2021.08); *A61F 2/748* (2021.08); *F16F 9/48* (2013.01); *F16F 9/512* (2013.01)

(58) Field of Classification Search
CPC ...... A61F 2002/5072; A61F 2002/6818; A61F 2002/6836; A61F 2002/745; A61F 2002/748; A61F 169/48; F16F 9/48
See application file for complete search history.

(56) References Cited

U.S. PATENT DOCUMENTS

| | | | |
|---|---|---|---|
| 5,957,981 A | 9/1999 | Finn | |
| 6,106,560 A | 8/2000 | Boender | |
| 6,113,642 A | 9/2000 | Petrofsky et al. | |
| 6,957,981 B2 | 10/2005 | Karino et al. | |
| 7,985,265 B2 | 7/2011 | Moser et al. | |
| 8,298,294 B2 | 10/2012 | Kaltenborn et al. | |
| 8,500,824 B2 | 8/2013 | Okuda et al. | |
| 8,628,585 B2 | 1/2014 | Harris et al. | |
| 8,951,304 B2 | 2/2015 | Wu | |
| 8,974,543 B2 | 3/2015 | Balboni et al. | |
| 8,986,398 B2 | 3/2015 | Poulson et al. | |
| 9,114,029 B2 | 8/2015 | Asgeirsson et al. | |
| 9,770,347 B2 | 9/2017 | Shen | |
| 2007/0233279 A1 | 10/2007 | Kazerooni et al. | |
| 2008/0255670 A1 | 10/2008 | Boiten et al. | |
| 2008/0262635 A1 | 10/2008 | Moser et al. | |
| 2009/0030530 A1 | 1/2009 | Martin | |
| 2010/0191347 A1 | 7/2010 | Pusch et al. | |
| 2013/0173022 A1 | 7/2013 | Arabian et al. | |
| 2014/0128993 A1 | 5/2014 | Shen | |
| 2014/0379096 A1 | 12/2014 | Zahedi et al. | |
| 2015/0134081 A1 | 5/2015 | Geiger et al. | |
| 2015/0305895 A1* | 10/2015 | Boiten .................... | A61F 2/604 623/26 |

FOREIGN PATENT DOCUMENTS

| | | |
|---|---|---|
| CN | 101959477 A | 1/2011 |
| CN | 103800102 A | 5/2014 |
| DE | 10 2012 023 023 A1 | 5/2014 |
| JP | 2008-246208 A | 10/2008 |
| JP | 2014-221093 A | 11/2014 |
| WO | 2014057086 A1 | 4/2014 |
| WO | 2016/100791 A1 | 6/2016 |

OTHER PUBLICATIONS

Murphy. Prosthetic Leg Kit for Deployement in Developing Countries. Figure 4. (Year: 2016).

* cited by examiner

PROSTHETIC JOINT WITH A MECHANICAL RESPONSE SYSTEM TO POSITION AND RATE OF CHANGE

CROSS REFERENCE TO RELATED APPLICATION

This application is a Divisional of U.S. patent application Ser. No. 15/536,240, filed 15 Jun. 2017 and titled "PROSTHETIC JOINT WITH A MECHANICAL RESPONSE SYSTEM TO POSITION AND RATE OF CHANGE" which claims the benefit of PCT/US2015/066614, filed 18 Dec. 2015, which claims the benefit of U.S. Provisional Application No. 62/094,009, filed 18 Dec. 2014, the disclosures of each of which are expressly incorporated herein by reference.

BACKGROUND

The field of prosthetics has seen many advances to enhance quality of life by improving mobility and returning functionality to persons suffering from injured or missing limbs. Prostheses attempt to mimic the movements of the limb that they replace. For example, a healthy functioning ankle will go through a series of plantarflexion and dorsiflexion motions during gait without the person having to consciously control the ankle movement. See FIG. 8. Therefore, improvements have been sought to produce prosthetic ankle joints that can mimic the movements of a healthy ankle to improve the patients comfort and functionality.

A prosthetic ankle joint must exhibit sufficient, but also controlled dorsiflexion and plantarflexion when the patient walks to permit the most natural gait possible. On the other hand, when the prosthesis user is standing, sufficient stability and support must be achieved to permit a stable stance. It is therefore necessary that the prosthesis is operated in two different states, namely for walking on the one hand and for standing on the other hand. To build the prosthesis lightweight, with little susceptibility to faults, low costs and energy-savingly, the prosthesis should be able to work without electronic control elements. It is also of benefit if the wearer of the prosthesis does not need to perform any unnatural movements to switch the prosthesis from one state into the other state, such as to switch the prosthetic joint, and particularly the prosthetic ankle joint, from the state "walking" to the state "standing" or vice versa. Even if the corresponding movements or movement patterns meet the purpose assigned to them, they appear unnatural in daily life and the user of the prosthesis may thereby be recognizable to bystanders as a prosthesis user in a potentially unpleasant manner.

DISCLOSURE OF THE INVENTION

The invention is therefore based on the problem of suggesting a prosthetic joint, and particularly a prosthetic ankle joint, as well as a procedure for its control that mitigates or removes the disadvantages named.

A prosthetic ankle joint design is disclosed that can provide functionality in two different states. In a first state, the joint is adapted to provide a dynamic, controlled-resistance walking gait, and in the second state, the joint is adapted to provide a static, fully supported standing state. The hydraulically regulated prosthetic joint enables both of these states without activation of each state through a microprocessor and without sacrificing standing stability in favor of a dynamically performing ankle during gait.

During walking gait, the healthy human ankle covers a range of about 30 degrees through a series of controlled dorsiflexion and plantarflexion periods. See FIG. 8. During standing, the ground-reaction-force (GRF) supporting body weight is located in the mid-food, and directionally travels to the anterior side of the ankle joint. This creates a moment on the ankle joint that must be counteracted to attain stability. In healthy ankles, the ankle is supported by the plantar flexor muscles. In mechanical prosthesis, it has been known to counteract the moment by a means of mechanical support, such as by a rigid attachment. In a hydraulically damped ankle allowing dorsiflexion with respect to the neutral position, this moment is not supported, leading to unstable and unsatisfactory performance of the ankle for the very common task of standing.

The prosthetic joint described herein has the advantage that the joint can be used as an ankle in one embodiment. The joint has a passive, mechanical response system to control the walking and standing states that mimics a naturally functional joint. The prosthetic ankle joint provides dorsiflexion and plantarflexion that mimics the movements of a natural ankle when walking and also provides support when standing.

A prosthetic joint according to the present invention comprises a first and second connector and a pivot device that allows the first and second connector to rotate with respect to each other, a first chamber and a second chamber, wherein the chambers are connecting via one or more fluid flow paths; an occlusion configured to restrict fluid flow between the chambers, and a non-electronic mechanism for controlling the flow, the mechanism being responsive to a position of the joint and/or a rate of change of position of the joint. Preferably the mechanism is arranged such that a dwell at a particular joint location or locations will occlude the flow path. Preferably the mechanism is responsive to both the position of the joint and the rate of change of this position.

The prosthetic joint or prosthesis joint preferably is a prosthetic ankle joint. The two connectors are connected pivotingly to each other via a joint that can take nearly any known form. These parts may, for example, be functional parts of the ankle joint, such as a sole part or an attachment element for a lower leg part, or additional elements to which further parts of the prosthesis joint can be attached. They are aligned with each other pivoting via an angle area that covers at least the area that is needed for the respective prosthesis joint, and particularly for the prosthetic ankle joint.

The two chambers are filled with a fluid and connected to each other flow-technically via the fluid connection. When the position of the joint is changed, i.e. when the first and the second connector are pivoted relative to each other, so that an enclosed angle changes, this will cause the fluid from one of the two chambers to flow into the respective other one. A specific position of the two connectors relative to each other is subsequently also called the joint position or location of the joint.

In a technically particularly simple version of the joint, the two chambers can be placed, e.g., on the two opposing sides of the actual joint. This way, one of the two chambers can be placed before the actual joint and one of the two chambers behind the joint. This is not mandatory, however. Before an behind means in the direction of the forefoot and in the direction of the heel, respectively, when the prosthetic joint is an ankle joint. These positions are called anterior and posterior to the joint or the pivot.

The occlusion can be formed as a throttle element or a closure element. It limits the amount of fluid that can flow through the fluid flow path. In every embodiment described here the occlusion can also be a valve.

The closure is controlled by a non-electronic control system or a non-electronic control device that reacts to the position of the joint and/or the speed of the change of position. In order to close the fluid connection, the joint must remain in a predetermined position or a predetermined position range for a predetermined period. This position preferably corresponds to the position that the joint holds when the wearer of the prosthesis of which the joint is a part is standing.

In this position, the control mechanism causes the occlusion to close the fluid connection if the joint remains in this position for a predetermined period. This is usually only the case when the patient is standing with the joint. When walking, the joint also goes through this position, but will not remain there for the predetermined duration, so that there will be no closing.

In one embodiment, the joint includes two hydraulic actuators acting in opposition on the joint on either side of a pivoting location. Hydraulic flow between the hydraulic actuators occurs through a passage. The passage can be open or occluded using a mechanical device, such as a cam linked to a valve. The joint is rotatably coupled to a foot. The joint response to walking and rotation of the foot is to adjust the resistance to flow between actuators as the foot experiences the ground reaction forces starting from heel strike, midstance, and push off. However, the resistance is not the same throughout the stance phase, but, varies with the rotational position and the rate of rotation.

The progression of dampening and of the resistance opposing the occurring force can be adjusted freely in a wide range by the shape of the cam connected to the valve.

In some embodiments, the joint comprises a bi-directional flow path with a variable occlusion that connects the chambers and a uni-directional flow path that connects the chambers, and further comprising applying a damping force on the occlusion when acted upon by the external forces to delay restriction to fluid flow.

In some embodiments, the joint comprises a bi-directional flow path with a variable occlusion that connects the chambers and a uni-directional flow path that connects the chambers, and further comprising wherein 100% of the forces that drive the occlusion to restrict flow are from the ground reaction forces.

However, it is also possible that with the embodiments described herein at least a part of the forces that drive the occlusion to restrict the flow stem from kinetic energy that is stored in appropriate devices for storing this energy. This can be elastic or resilient elements such as elastomers and springs.

In some embodiments, the joint includes a cam driving a follower; the follower position drives closure of an occlusion, preferably of a valve against an opposing damping element to restrict fluid flow.

In some embodiments, the cam induces a dwell period during at least one portion of rotation during which the cam drives the occlusion to fully close at or before the mechanism dynamics cease. Preferably the occlusion is a valve.

In some embodiments, the joint includes a magnetic element; wherein the magnetic element drives the closure of a valve against an opposing damping element to restrict fluid flow.

In some embodiments, a magnetic force at a predetermined joint location fully closes the valve at or before the closure mechanism reaches a steady-state.

In some embodiments, fluid transfer is restricted when standing at a particular angle of the joint for a period of time determined by a damping element.

In some embodiments, when a center of gravity of a body supported by the joint is anterior of the pivot location, and the mechanism has occluded the flow path, the rate of rotation is zero.

In some embodiments, the occlusion is connected to a damping element that opposes movement of the occlusion when the occlusion moves to restrict fluid flow between chambers.

In some embodiments, the joint further comprises a cam driving a follower, the follower position drives closure of the occlusion through a compliant element.

In some embodiments, the cam shape provides simple harmonic motion.

In some embodiments, the cam and occlusion mechanism are configured to occlude the passage between anterior and posterior cylinders when the joint is stopped, or nearly stopped, at a particular angular location for a period of time defined by the mechanism dynamics.

In some embodiments, the joint includes a magnetic element; wherein the magnetic element drives the closure of the occlusion against an opposing damping element.

In some embodiments, a magnetic force at a predetermined joint location fully closes the valve at or before the mechanism reaches a steady state.

In some embodiments, the joint comprises a bi-directional flow path connecting the first and second chambers.

In some embodiments, the joint comprises a uni-directional flow path connecting the first and second chambers.

Preferably, the joint has at least one piston that is at least partially placed in the first chamber and/or in the second chamber, the at least one piston being moved by movement of the first connector relative to the second connector so that fluid from one chamber is moved to the other chamber. It is of advantage if fluid is moved from the first chamber into the second chamber during a movement of the joint into one direction, e.g. at dorsiflexion, while fluid will be moved from the second chamber into the first chamber in the opposite movement of the joint, i.e. plantarflexion.

It is of advantage for the joint to have precisely one piston that is placed partially in the first chamber and partially in the second chamber. This may, e.g., be formed as a circular ring segment, and have two ends, each of which protrudes into one of the two chambers. By moving the piston relative to the two chambers, there will be a volume change, with the volume in one of the two chambers reducing and the volume of the respective other chamber increasing. This causes the fluid in the chambers to be moved through the fluid connection.

It has turned out to be beneficial if the dampening element against which the closure can be moved into the closed position, is also a hydraulic or pneumatic dampening element or a dampening element filled with a different fluid. Thus, the closure can be, e.g., a needle valve the needle of which is pushed into the fluid connection to close the fluid connection and to put the valve from the "walking" to the "standing" mode. For this, a part of the valve to which the needle belongs, must be pushed into a volume that has a fluid connection to a dampening chamber and a dampening piston. Preferably, the dampening element has at least one dampening chamber and at least one dampening piston, which is actuated in a predetermined range of the position of the first connector relative to the second connector to prevent closing of the fluid connection.

The fluid connection between the one area or volume of the closure and the dampening chamber can be used to set the strength of the dampening applied by the dampening element. A throttle valve or similar device may be present for this as well. The dampening piston that closes the dampening chamber off to one side may have an actuation element that may interact with the cam or an element attached to it. This is particularly of benefit when a large force is applied to the closure in an extreme position of the joint, i.e. at strong pivoting of the first connector relative to the second connector, which alone would be sufficient to close the fluid connection between the first chamber and the second chamber relatively quickly. Since this may not be desired in this position, however, there may be an actuation element at the dampening piston for this case. The dampening piston is then pushed towards the dampening chamber and thus pushes the fluid in it through the further fluid connection towards the closure, thus preventing closing of the fluid connection between the two chambers.

In some embodiments, a prosthetic system includes the prosthetic joint of any of the above embodiments, a prosthetic foot connected to the joint at one of the connectors, and the second connector is connected to a prosthetic device. Preferably this device includes a socket to receive a limb.

In some embodiments, a method of controlling rotation of a prosthetic joint includes applying an external force that causes rotation of a joint wherein the joint comprises a first and second chamber; transferring fluid between the first and second chambers in response to rotation of the joint; providing a feature to occlude or partially occlude the fluid between chambers; providing a non-electronic mechanism for controlling the flow responsive to a position of the joint and/or a rate of change of position of the joint. Preferably the mechanism is arranged such that a dwell at a particular joint location or locations will occlude the flow path.

In some embodiments, a method of controlling dorsiflexion and plantarflexion of a hydraulic prosthetic ankle joint, includes generating ground reaction forces with a hydraulic prosthetic ankle, wherein the prosthetic hydraulic ankle comprises a first chamber and a second chamber, and the ankle is connected to a prosthetic foot; rotating the prosthetic foot in response to the ground reaction force; transferring fluid between the first chamber and the second chamber in response to rotation of the foot; providing a feature to occlude or partially occlude the fluid transfer between chambers; providing a non-electronic mechanism for controlling the flow responsive to a position of the joint and/or a rate of change of position of the joint. Preferably the mechanism is arranged such that a dwell at a particular joint location or locations will occlude the flow path.

Preferably, the fluid flow path can be opened again in the method by application of a torque onto the first connector or the second connector in a predetermined direction. This way, it is particularly easily possible to return the joint from the operating mode or state "standing" to the operating mode or state "walking".

Preferably, a force is applied by means of the torque onto the fluid that is thus moved by the one-way connection from one chamber to the respective other chamber, which releases the lock applied by the closure.

In a preferred embodiment the first and second chambers are located anterior and posterior to a joint or pivot. In this context this of course means that only one chamber is positioned anterior to the joint and the other chamber is positioned posterior to the joint.

The embodiments of the joint rely on the use of a non-electronic mechanism for controlling the flow responsive to both a position of the joint and a rate of change of position of the joint, wherein the mechanism is arranged such that a dwell at a particular joint location or locations will occlude fluid flow. The mechanisms can operate fully by the ground reaction forces, such as when walking, standing, or sitting, for example, or from changing positions. A mechanism that can control fluid flow via the use of non-electrical components may reduce the overall size due to elimination of a power source.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

BEST MODE(S) FOR CARRYING OUT THE INVENTION

Figure 1:
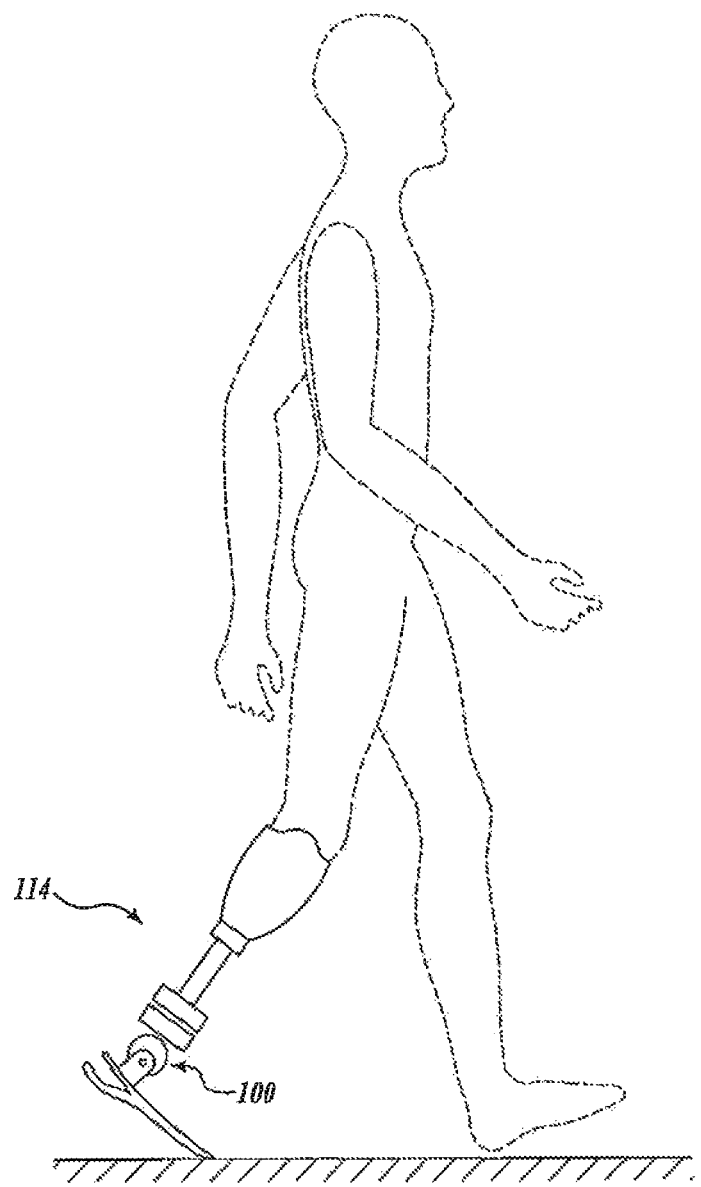
FIG. 1 is a diagrammatical illustration representing one embodiment of an application for the joint described herein.
Figure 2:
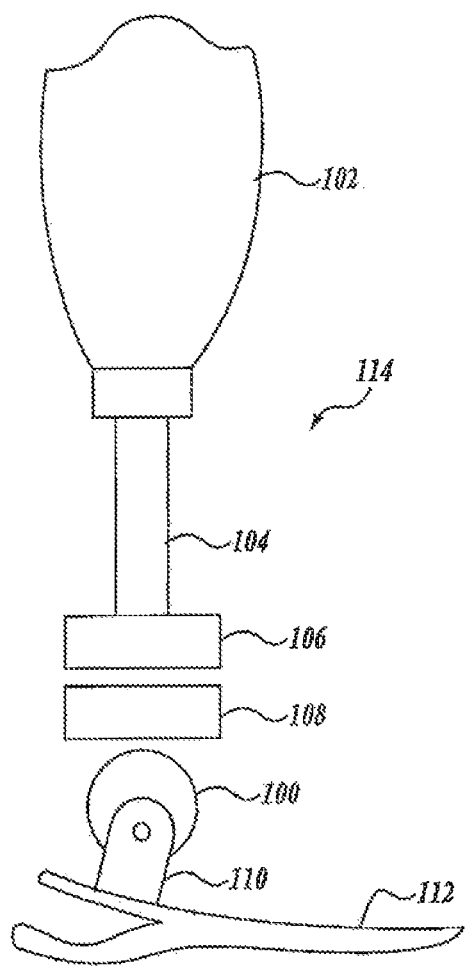
FIG. 2 is a diagrammatical illustration of a prosthesis representing one embodiment of an application for the joint described herein.

Referring to FIG. 1, a diagrammatical illustration of a person wearing a below-the-knee prosthesis 114 with an ankle joint 100 is illustrated. In FIG. 2, the below-the-knee prosthesis 114 includes a socket 102 for receiving the amputated limb, a shank (or pylon) 104 connecting the base of the socket to a connector 106. The connector 106 can be the "inverted pyramid" connector. The connector 106 is received within a receiver 108. The receiver 108 can have set screws that lock the connector 106 in place. The receiver 108 is then connected to the joint 100, which in turn is connected to a prosthetic foot 112 via a hinge 110. The socket 102, shank 104, connector 106, and foot 112 can all be well-known components. The joint 100 is illustrated functioning as an ankle, however, the joint can have other applications, such as a knee or hip joint.

Figure 3:
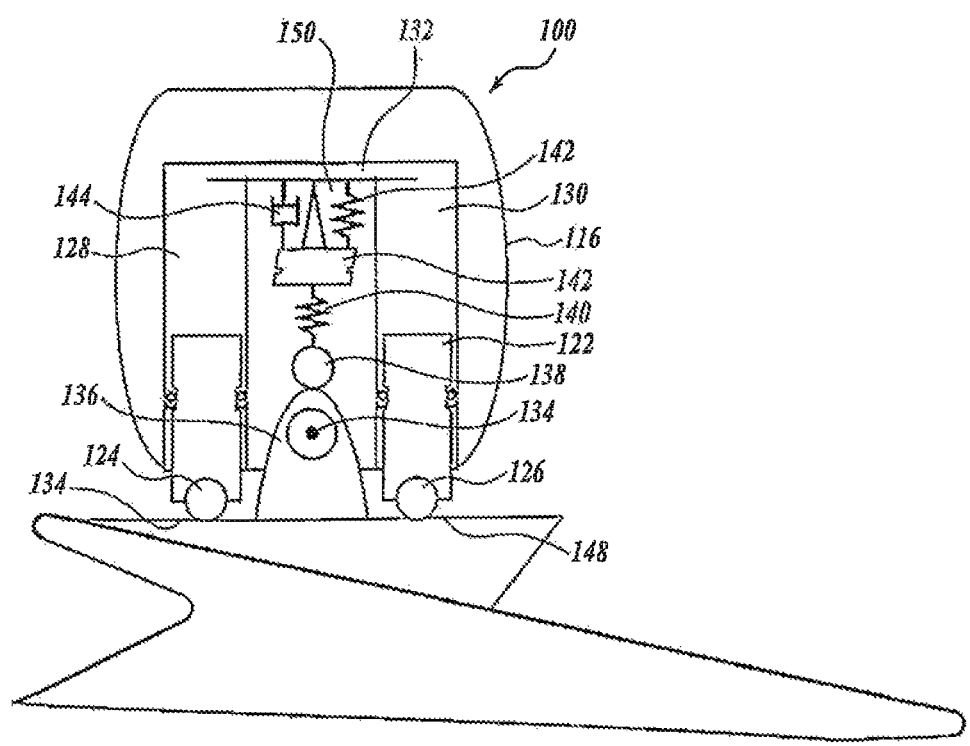
FIG. 3 is a diagrammatical illustration of a joint in accordance with one embodiment.

Referring to FIG. 3, a prosthetic joint 100 suitable to be used as the ankle joint 100 in FIGS. 1 and 2 is illustrated. The joint of FIG. 3 is highly schematic to illustrate major components of one embodiment of the prosthetic joint. The joint 100 includes an outer hydraulic case 116. The case is provided with an interior first chamber 128, an interior second chamber 130, a first piston 120 within the first chamber 128, and a second piston 122 within the second chamber 130. The chambers 128 and 130 are filled with a hydraulic fluid. A passage 132 between the first chamber and the second chamber is provided. The first piston 120 and the second piston 122 each includes a cam follower 124 and 126, respectively, that rests on cams 118, 148. The prosthetic joint 100 is rotatably connected to the foot 112 via a pivot 134. The foot may dorsiflex and plantarflex with respect to the joint 100 about the pivot 134. The foot is driven to rotate by engaging in a walking gait motion, for example. Of course, the first piston 120 and the second piston 122 can also be two ends of only one piston which can be shaped in form of a part of a ring. It is also possible to use only one cam.

In one embodiment, a cam assembly is provided to regulate or stop the flow between chambers. The cam assembly can provide controlled dorsiflexion and plantar flexion when walking and also provide stability when standing without the use of electronics. Other embodiments can use a magnetic device to regulate and stop the flow.

Figure 4:
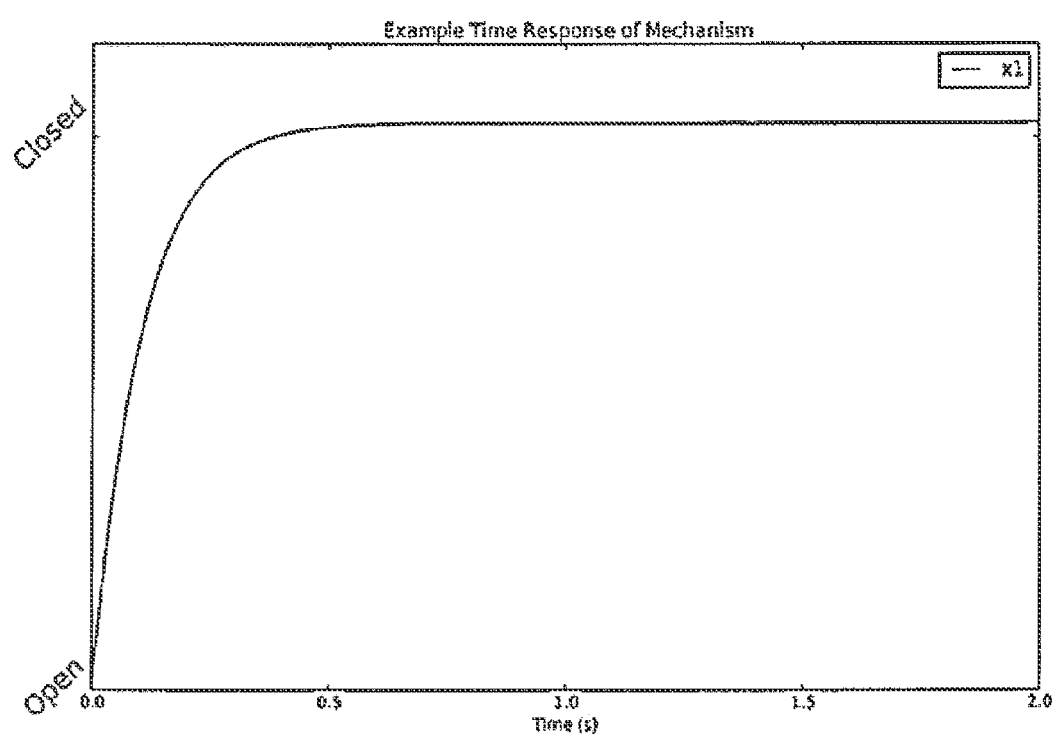
FIG. 4 is a time response graph plotting time verses percent of closure during standing for one embodiment of a joint.

The cam assembly may include a cam 136, a follower 138 in contact with the cam surface, a primary spring 140 that is connected between the follower and the lever arm 142. The lever arm is connected to a damping device 144 and a secondary spring 146 that opposes the damping device. The lever arm is also connected to an occlusion 150. The occlusion 150 is configured to variably block the passage 132 between chambers 128 and 130. This passage 132 is the fluid flow path between the two chambers 128, 130. Thus, with the increasing blockage, the resistance to fluid flow between chambers increases until the occlusion 150 fully blocks the passage 132 and fluid transfer between chambers 128 and 130 is stopped so the ankle becomes locked into position. The amount of restriction to fluid flow can depend on the shape and configuration of the cam 136. In one embodiment, less resistance occurs the greater the plantarflex or dorsiflex angle is or becomes. Greater resistance occurs as the angle (between foot and shank, for example) approaches zero or near zero, corresponding to midstance or when the body's center of gravity is in line with the center of rotation of the joint. The occlusion is damped so that a faster gait results in less resistance to flow compared to a slower gait which increases the resistance. The damping reaction can be adjusted to be slower or faster based on the user of the joint. The cam 138 can be symmetric or asymmetric with respect to the nose of the cam. The cam sides can be linear or nonlinear and can define an involute shape. The nose of the cam 138 is the top or maximum point of the cam from the point of rotation. The lobe length is defined as the length between the point of rotation to the nose. The dimensions and placement of the cam 138 and the shape can be modified to fit a particular user of the joint to coincide with the user's walking characteristics. In order to effectuate the standing state, the cam 138 is adjusted such that when the angle of the ankle is at or near zero, corresponding to at or about midstance, and the rate of rotation is at or near zero, corresponding to standing still, then the cam 138 can line up to exert the maximum lift on the occlusion 150 and coupled with the damping response will fully restrict the flow between chambers 128, 130 to support the joint in the standing position. Resuming a walking gait will move the cam 138 out of maximum lift and allow the occlusion 150 to permit flow between chambers once again. FIG. 4 shows a graph of one embodiment of the response of a joint at steady state occurring when a person is standing still, i.e., when the rotation angle is at or near pre-selected zero and the rate of rotation is at or near zero. As the graph shows, the fully closed position is reached in about 0.5 seconds or less. However, it is to be appreciated that the response of the joint can be changed depending on the intended user of the joint.

Figure 5:
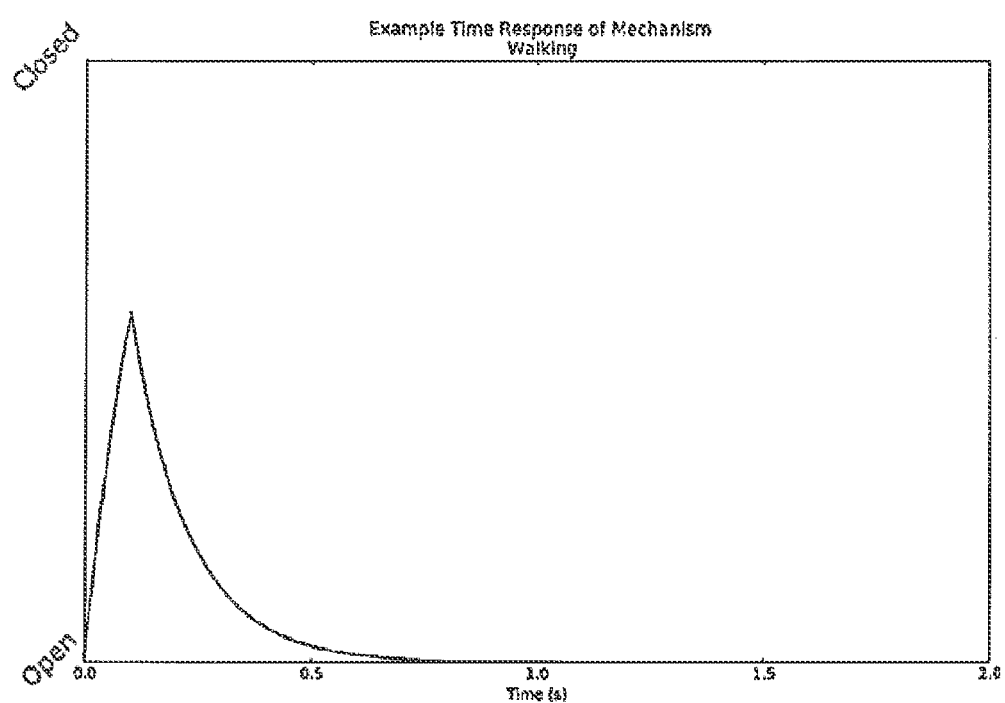
FIG. 5 is a time response graph plotting time verses percent of closure during walking for one embodiment of a joint.
Figure 8:
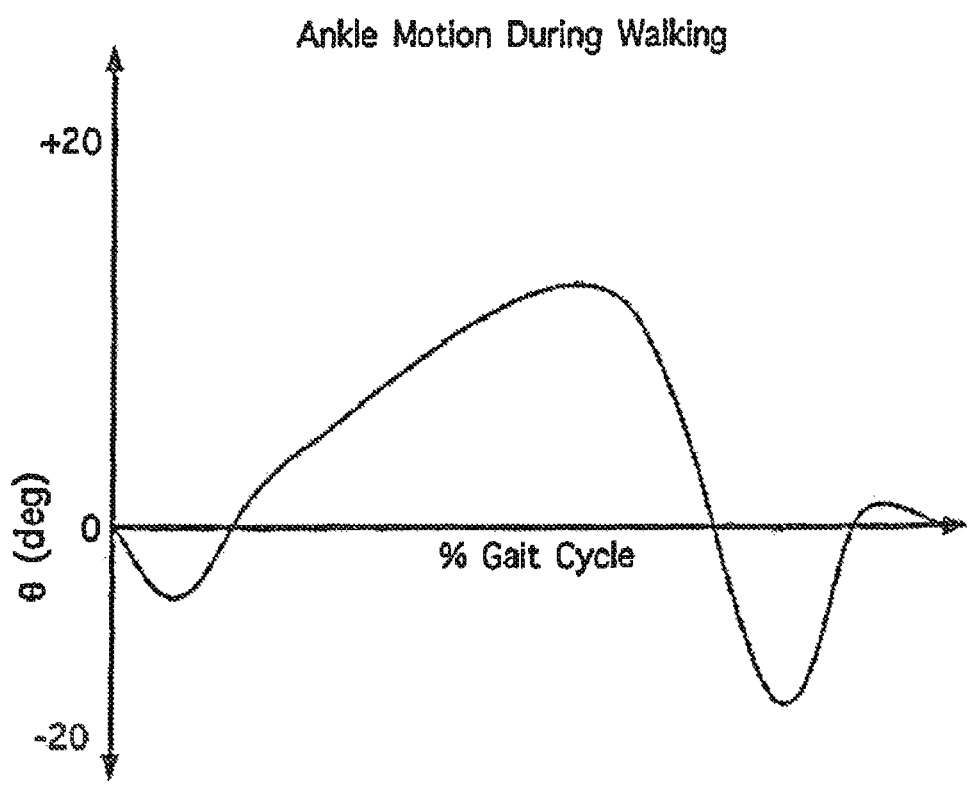
FIG. 8 is graph of plantarflexion and dorsiflexion of a healthy joint.
Figure 9:
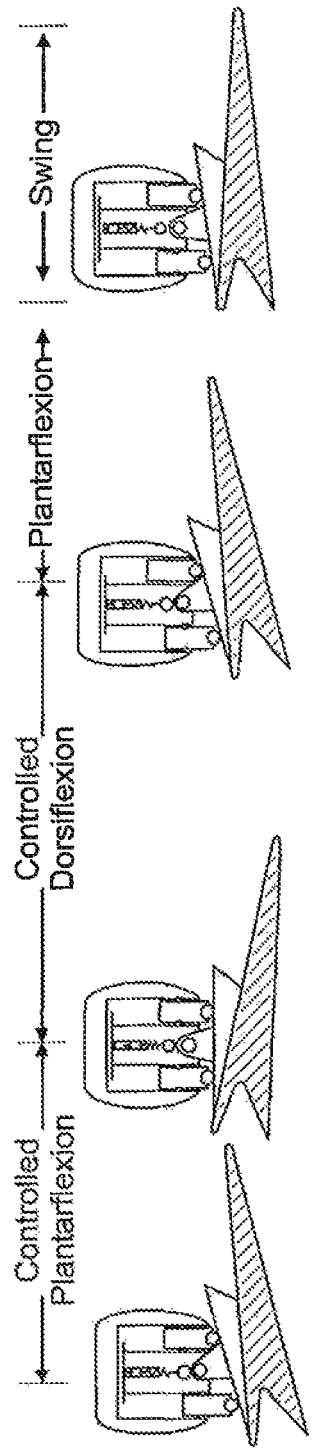
FIG. 9 is a diagrammatical illustration of a joint in accordance with one embodiment in different phases of the gait cycle.

The foot rotates in relation to the joint via the application of external forces, such as the ground reaction forces. A walking gait includes the stance and swing phase. The stance phase, i.e., when any part of the foot is in contact with the ground, begins with heel strike when the end of the heel first strikes the ground. This causes a slight plantarflexion movement initially, as shown in FIG. 8 as a negative rotation. As the stance phase continues, dorsiflexion occurs, the angle becomes zero approximately at midstance. However, zero angle is relative and can vary between persons. Dorsiflexion continues to a maximum after midstance, and is followed by planterflexion in preparation for toe-off. plantarflexion reaches a maximum at toe-off. Then, dorsiflexion occurs to lift the toe during swing phase to avoid stubbing the toe into the ground, and can end with the angle approximately at zero in preparation for the next cycle. See FIG. 9 for the controlled phases of planterflexion and dorsiflexion of the joint. FIG. 5 plots the time versus the percent opening between chambers. As can be appreciated, the aim is for the valve to never fully close 100% and remain open throughout a walking gait.

Figure 6:
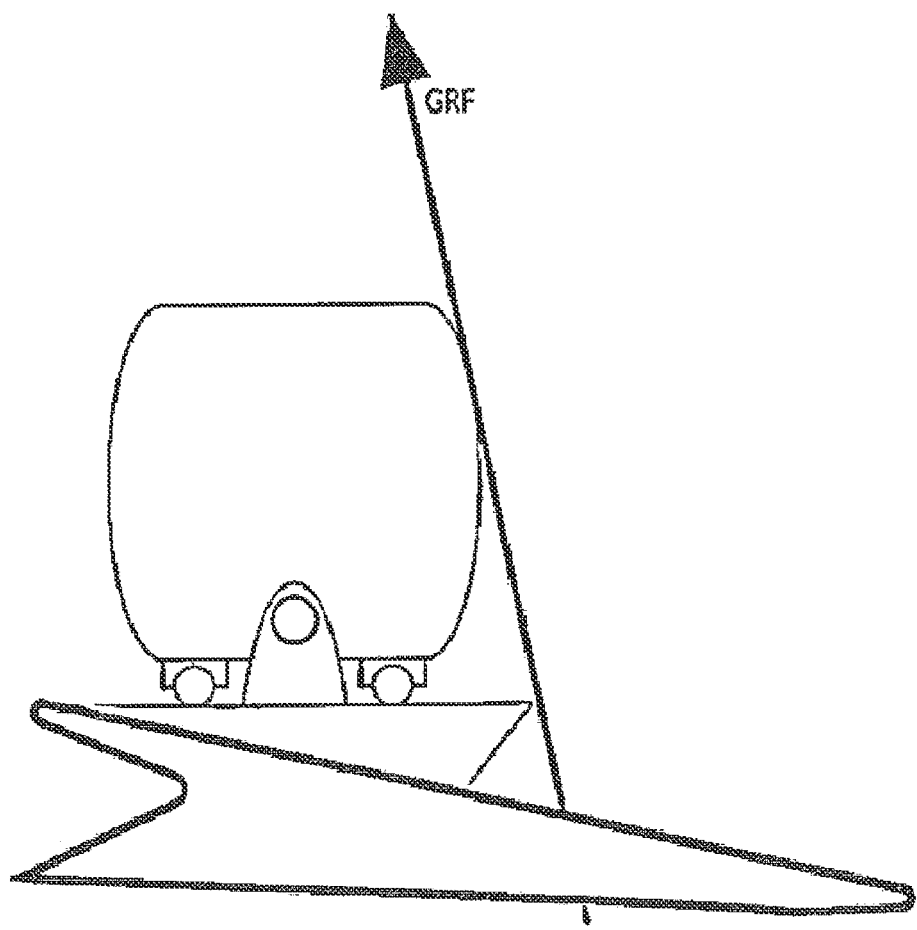
FIG. 6 is a diagrammatical illustration of a joint in accordance with one embodiment with the ground reaction force during standing.
Figure 7:
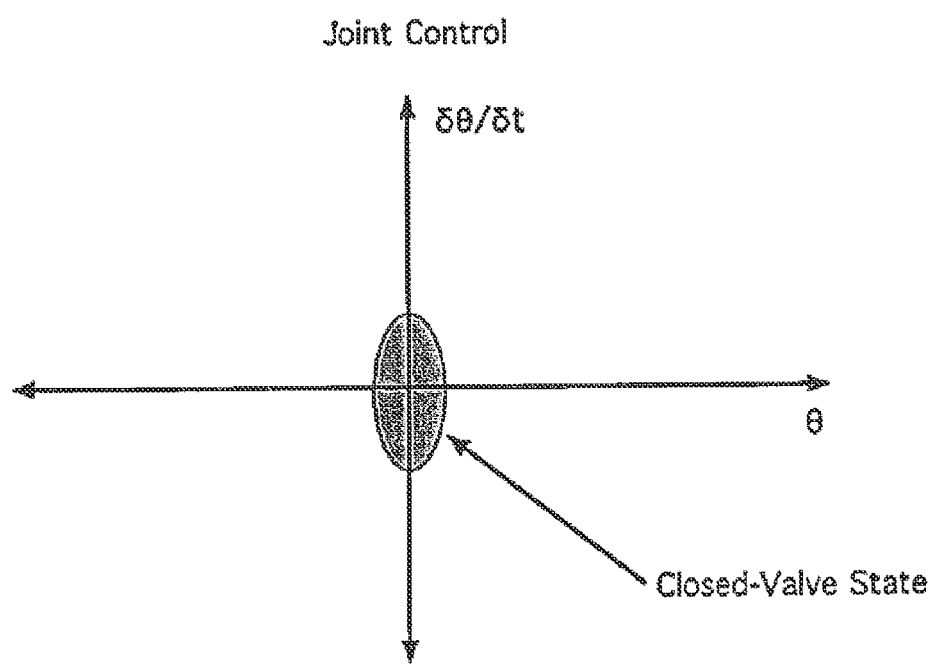
FIG. 7 is an illustration of a state space diagram for a joint in accordance with one embodiment.

As mentioned in the Summary section, an ankle joint needs to respond to a walking gait and a standing steady state. The steady state occurs when the body is standing still as illustrated in FIG. 6. The ground reaction force tends to dorsiflex the ankle. However, upon acquiring the standing position, the cam 138 exerts close to or the maximum lift on the occlusion 150. That is, where the angle of rotation is at or near zero and the rate of rotation is also approximately zero, the occlusion 150 will close the channel, thus locking the ankle at that position. FIG. 7 represents the steady state or the closed-valve state of the ankle. The horizontal axis is the degree of rotation, where negative is plantarflexion and positive is dorsiflexion, and the vertical axis is the rate of change of rotation. The ellipse in FIG. 7 represents the conditions where the valve is closed. When standing at a neutral position (where theta is near zero), and the velocity of the joint is also near zero, then, the valve will close to provide full support of the ground reaction force induced moment. When passing through the neutral position during walking, the rate of rotation of the joint is great enough to avoid closing the valve. That is, when walking, the rate of rotation is never small enough to allow the valve to fully close due to the delay of the damping device.

Figure 10:
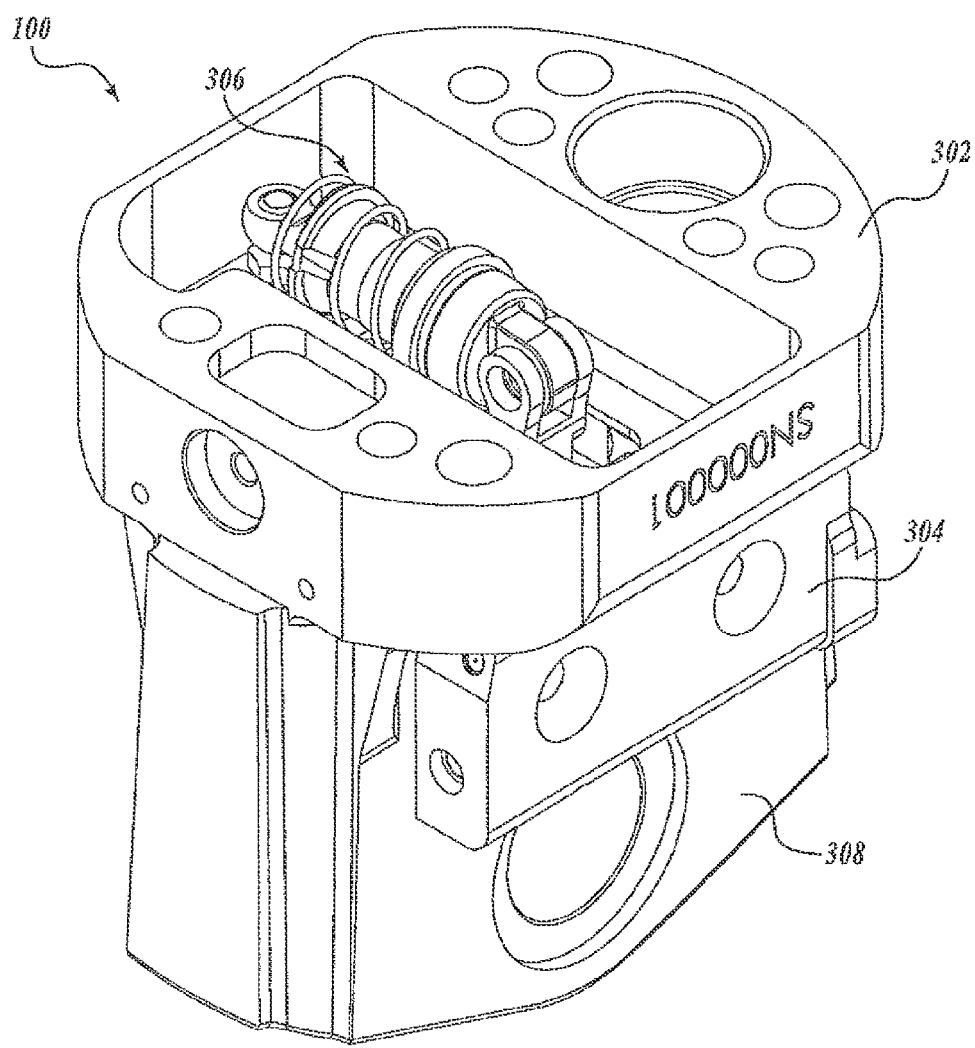
FIG. 10 is a diagrammatical illustration of portions of a joint in accordance with one embodiment.

Referring to FIG. 10, one embodiment of a joint 100 is illustrated. The joint 100 includes a hydraulic case 308, a valve 304, a receiver 302, and a cam assembly 306. The joint includes an aperture for receiving a pivot axle.

Figure 11:
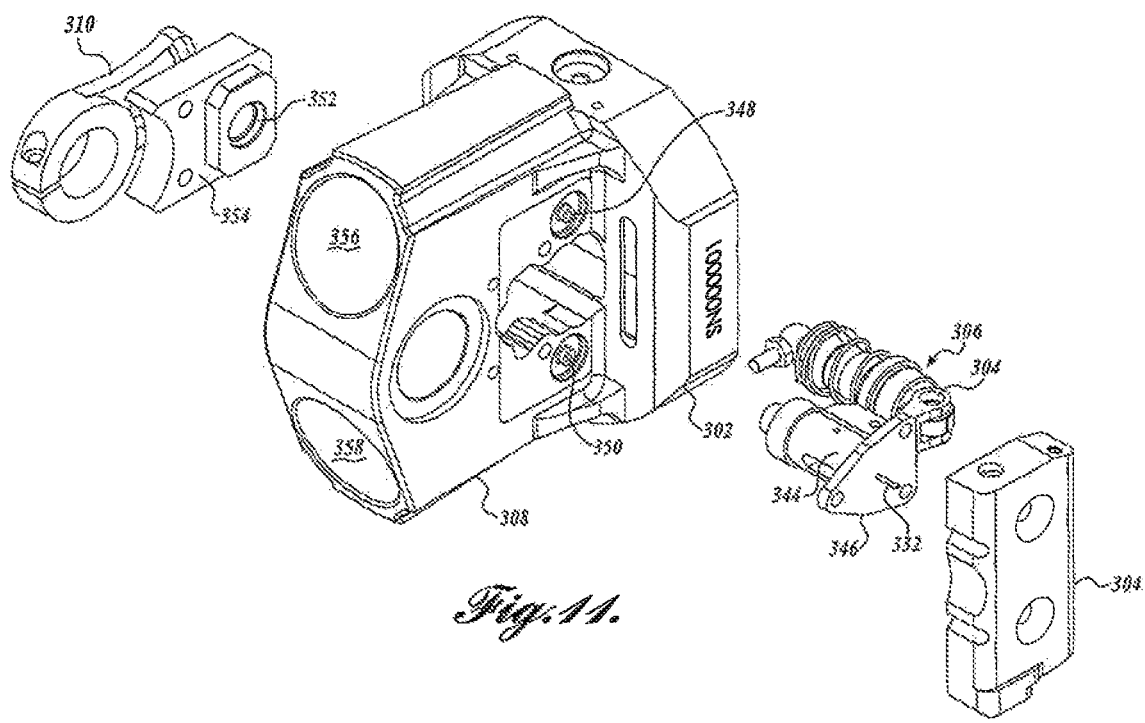
FIG. 11 is a diagrammatical illustration of portions of a joint in accordance with one embodiment.
Figure 12:
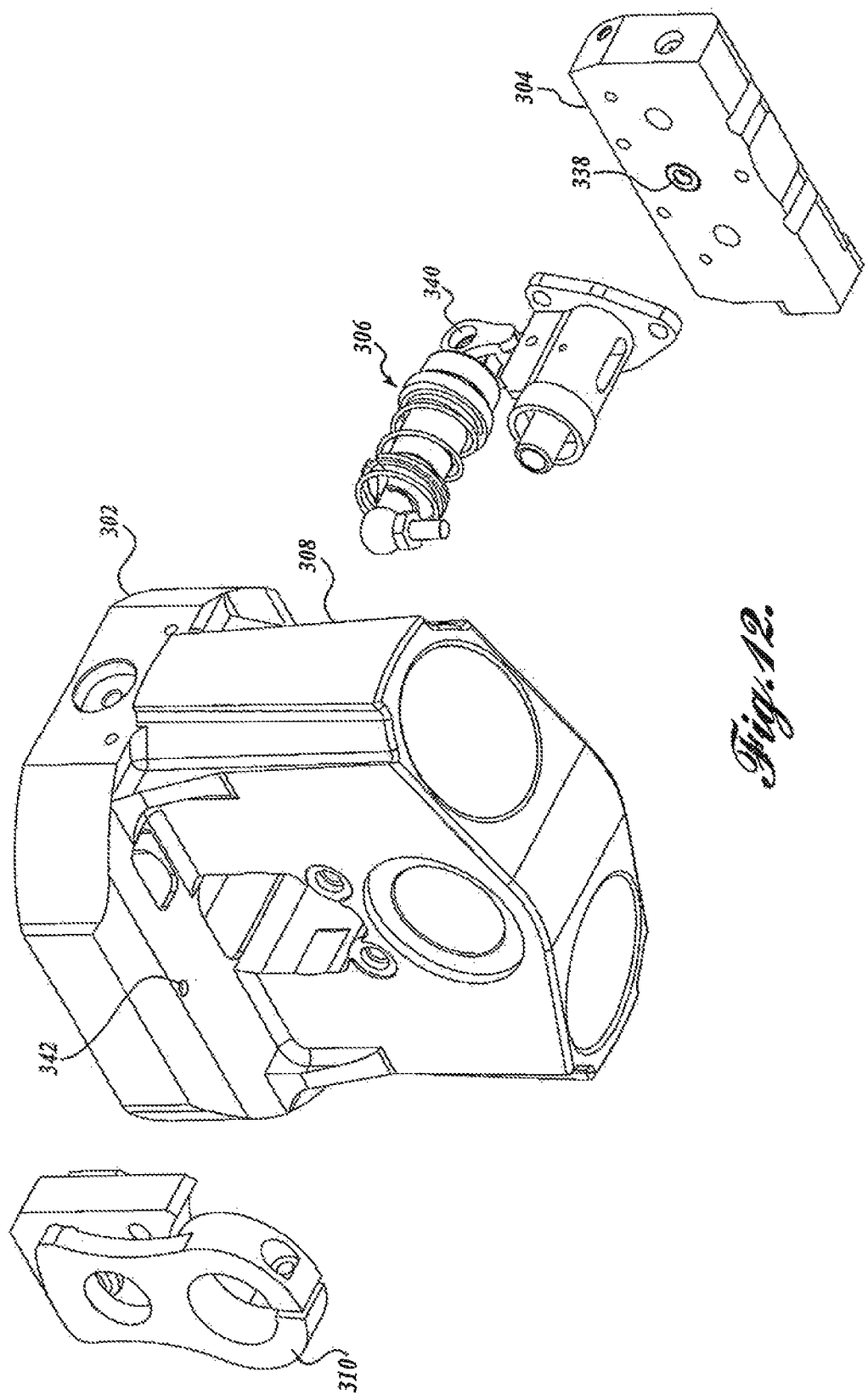
FIG. 12 is a diagrammatical illustration of portions of a joint in accordance with one embodiment.

FIGS. 11 and 12 more clearly show the major parts of the joint 100 and their placement on the joint 100. The valve 304 can be the valve disclosed in U.S. application Ser. No. 14/213,293, filed on Mar. 14, 2014. The hydraulic case 308 with pistons and channels can be similar to the ankle joint body 104 with pistons and channels described in U.S. Patent Application Publication No. 2013/0173022, with the modifications noted herein. Both applications are incorporated herein expressly by reference.

The modifications to the hydraulic system described in U.S. Patent Application Publication No. 2013/0173022 include the removal of electronics that activate the hydraulic system and modifications to allow placement of the cam assembly 306 described herein. The joint described herein, can have electronic sensors, such as accelerometers and angle sensors, for example.

Figure 13:
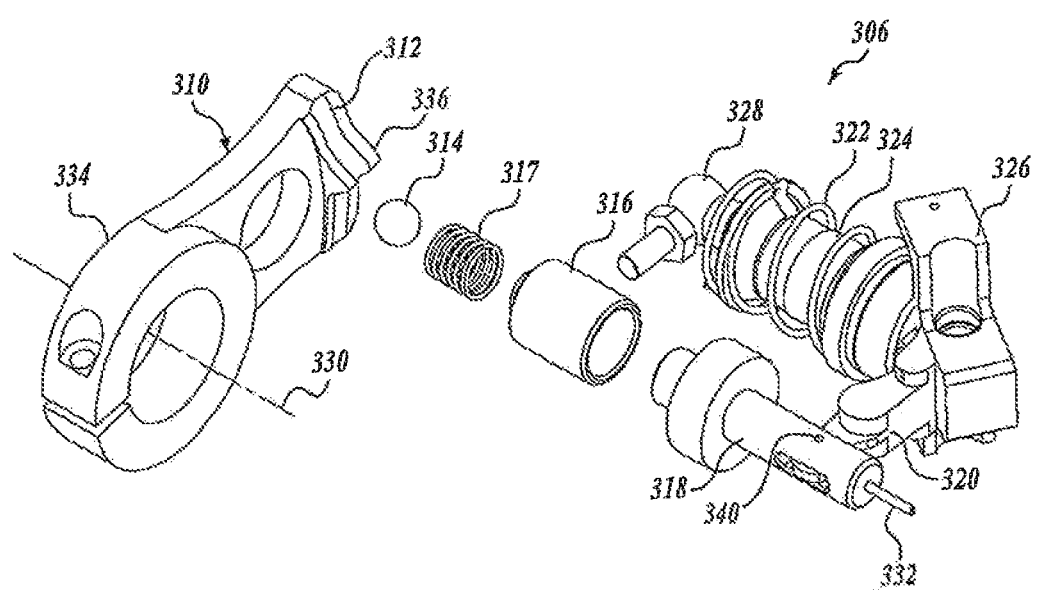
FIG. 13 is a diagrammatical illustration of portions of a joint in accordance with one embodiment.

Referring to FIG. 13 the cam assembly is shown. The cam 310 is connected to a pivoting axle, for example, that pivots about the axis of rotation 330. The cam has a clamp 334 to connect to the pivoting axle. The cam includes a cam surface 312 that lies generally on a plane perpendicular to the line of rotation. The cam surface has a nose 336 that reaches a maximum lift. The cam assembly has a cam follower comprising a roller ball 314, a spring 317, a sleeve 316 and a plunger 318. The ball 314 is held m the sleeve 316. The ball 314 contacts the spring 317, which in turn contacts one end of the plunger 318. The opposite end of the plunger has a pin 332, generically referred to an "occlusion" here. The pin 332 fits into the aperture 338 on the valve 304 shown in FIG. 12. The depth of the pin within the aperture 338 of the valve will determine not only the direction of flow, but, also the resistance to flow. As the ball 314 rides over the cam surface, the depth of the pin 332 can be influenced based on the characteristics of the spring 315. The plunger 318 forward movement into the valve is also counteracted by a spring 322, and damping device 324 dampens the forward movement of the plunger. The plunger is connected to a lever arm 320 at location 340 as shown on FIG. 11 or 12. The opposite end of the lever arm is connected to a damping device. The damping device is then connected via the pin 328 to a hole 342 in the hydraulic case 308.

Referring to FIGS. 11 and 12, the damping assembly 306 fits into the hydraulic case 308 within the cavity 360. The plunger 318 is enclosed in a shroud 344. The pin 332 projects through a plate 346, such that the pin is aligned with the aperture 338 of the valve 304. The hydraulic case 308 has ports 348 and 350, each one respectively leading to a chamber 356 and 358. The ports 348 and 350 are bi-directional to allow hydraulic fluid both into and out of the chambers and the valve 304.

In FIG. 11, the ball 314 of the cam follower fits into the hole 352 of the ball receptacle 354. The ball 314 projects out of the ball receptacle 354 to ride on the cam surface. The receptacle 314 contains a spring 317 therein, and the spring 317 rests against one end of the plunger 318.

Via the mechanism described, the direct motion of the ball 314 is decoupled to the valve open/closure by the spring 317. The spring 317 is part of the decoupling action. Because of the damping element resisting the first spring 317, the system will not respond instantaneously. This allows the valve to stay open during walking even though the cam follower passes a high position.

However, when standing at the location of the high dwell, the damping element yields (in time) to the first spring 317 and the valve closes shutting off hydraulic fluid transfer. The amount of time this takes is tunable by the rate coefficient of the damping element.

Figure 14:
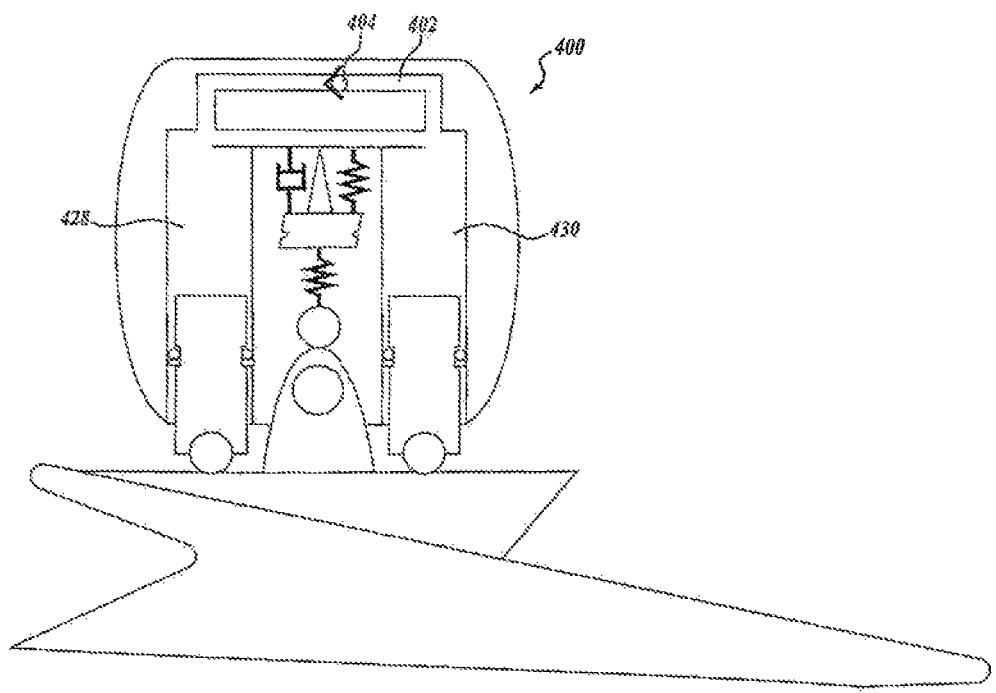
FIG. 14 is a diagrammatical illustration of a joint in accordance with one embodiment.

FIG. 14 is a second embodiment of the prosthetic hydraulic joint shown in FIG. 3, however, the joint of FIG. 4 includes a hydraulic fluid path 402 with a one-way valve 402 connecting the first hydraulic chamber 430 to the second hydraulic chamber 428.

Figure 15:
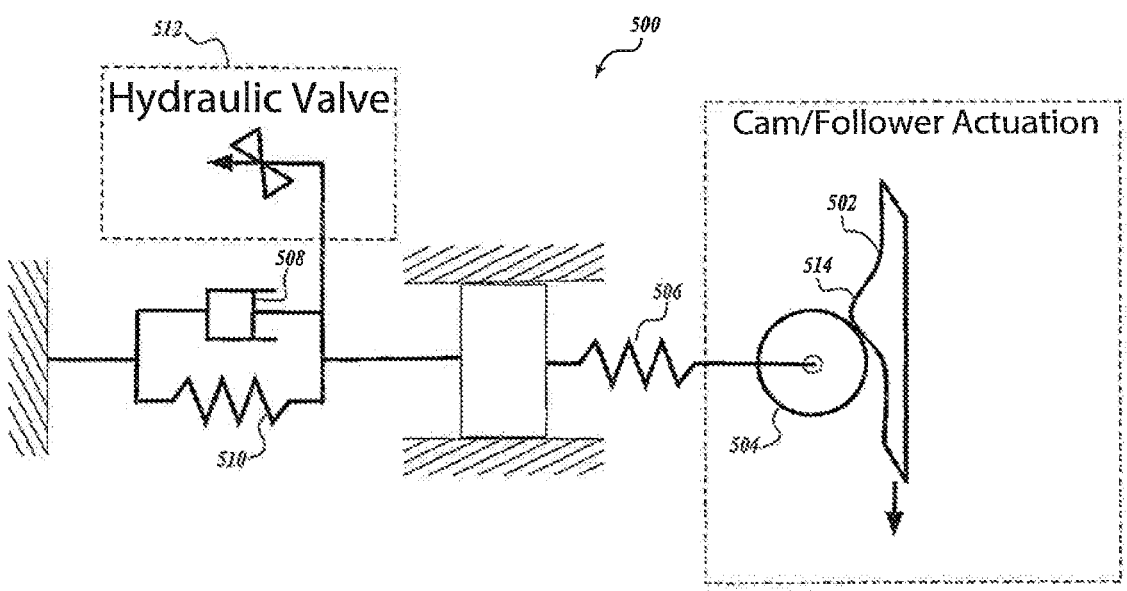
FIG. 15 is a diagrammatical illustration of a non-electrical mechanism in accordance with one embodiment.

FIG. 15 is a schematic illustration of a non-electronic mechanism 500 for controlling the flow responsive to both a position of the prosthetic joint and a rate of change of position of the joint and the mechanism is arranged such that a dwell at a particular joint location or locations will occlude fluid flow. A specific mechanism has already been described in connection with FIGS. 10-13 above. However, the mechanisms are not thereby limited. FIG. 15 is representative of a non-electronic mechanism using a cam surface 502 in contact with a cam follower 504. The cam surface can be dictated, in part, by the gait characteristics of the particular user. The cam follower 504 is in contact with a first spring 506, which in turn is in contact with a damping element 508 and a second spring 510. The mechanism operates a valve 512 to control the hydraulic flow between a first chamber and second chamber of the prosthetic joint, such as the joints that are illustrated in either FIG. 3 or FIG. 14. As can be appreciated, the cam follower 504 generally being at the location of the high dwell 514 of the cam surface 502 is configured to coincide when a person with the joint is standing. Given sufficient time at the high dwell location, the damping element 508 yields to the first spring 506 and the valve 512 closes shutting off hydraulic fluid transfer. The amount of time this takes is tunable by the rate coefficient of the damping element 508.

Figure 16:
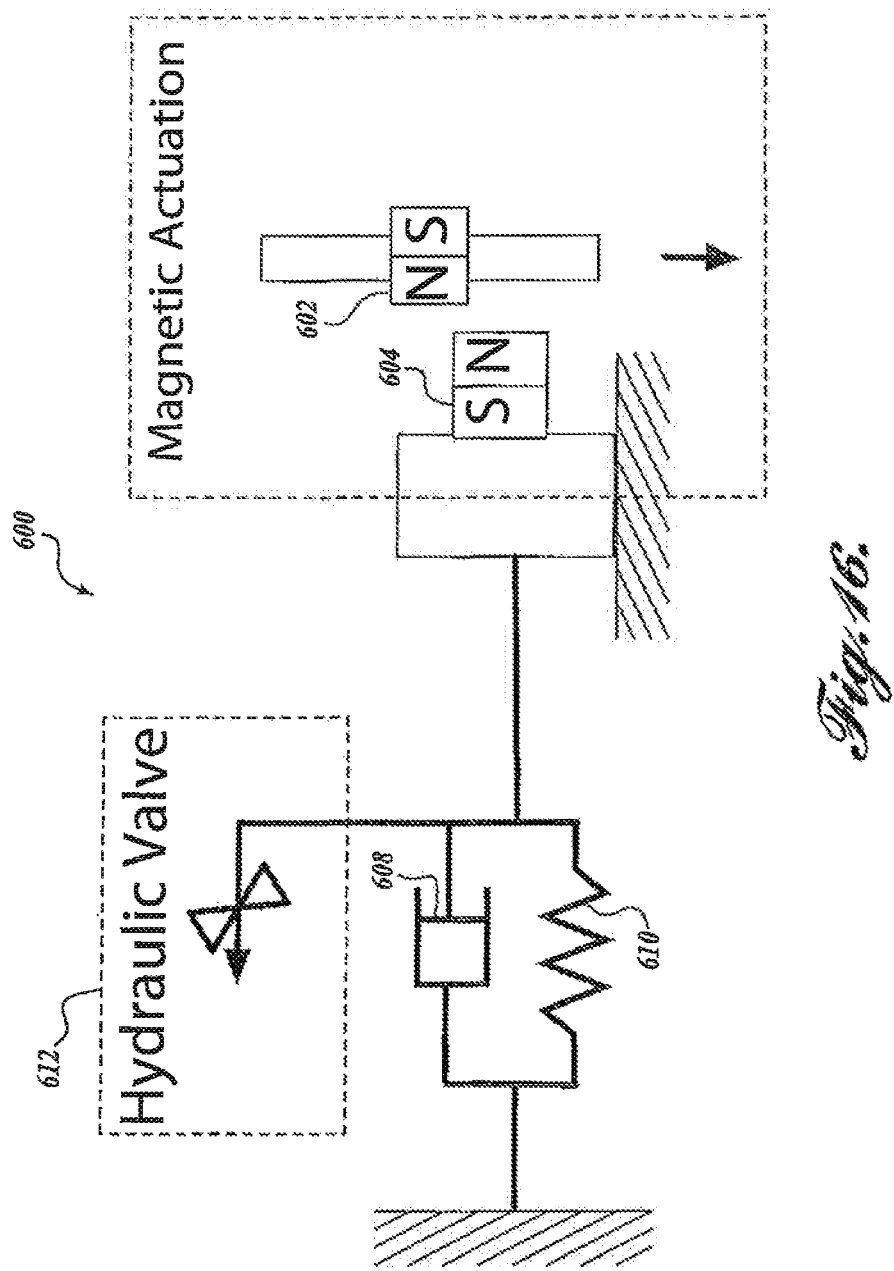
FIG. 16 is a diagrammatical illustration of a non-electrical mechanism in accordance with one embodiment.

FIG. 16 is a schematic illustration of a non-electronic mechanism 600 for controlling the flow responsive to both a position of the joint and a rate of change of position of the joint and wherein the mechanism is arranged such that a dwell at a particular joint location or locations will occlude fluid flow. A specific mechanism has already been described in connection with FIGS. 10-13 above. However, the mechanisms are not thereby limited. FIG. 16 is representative of a non-electronic mechanism using a first magnet 602 moving in proximity to a second magnet 604. The first magnet 602 moves back and forth along the direction indicated by the arrow. The second magnet 604 moves perpendicular to the motion of the first magnet. As can be appreciated, when the north (or south) pole of the first magnet is aligned in closest proximity to the north (or south) pole of the second magnet, the greatest repulsion force will be realized. In other configurations, the attraction force may also be used. The second magnet 604 is in contact with a damping element 608 and a spring 610. The mechanism operates a valve 612 to control the hydraulic flow between a first chamber and second chamber of the prosthetic joint, such as the joints that are illustrated in either FIG. 3 or FIG. 14. As can be appreciated, the magnets generally being at the greatest repulsion force (or attraction force) is configured to coincide when a person with the joint is standing. Given sufficient time at the greatest repulsion (or attraction force), the damping element 608 yields to the spring 610 and the valve 612 closes shutting off hydraulic fluid transfer. The amount of time this takes is tunable by the rate coefficient of the damping element 608.

While a preferred embodiment of the invention has been illustrated and described, it will be appreciated that various changes can be made therein without departing from the spirit and scope of the invention.

Figure 17:
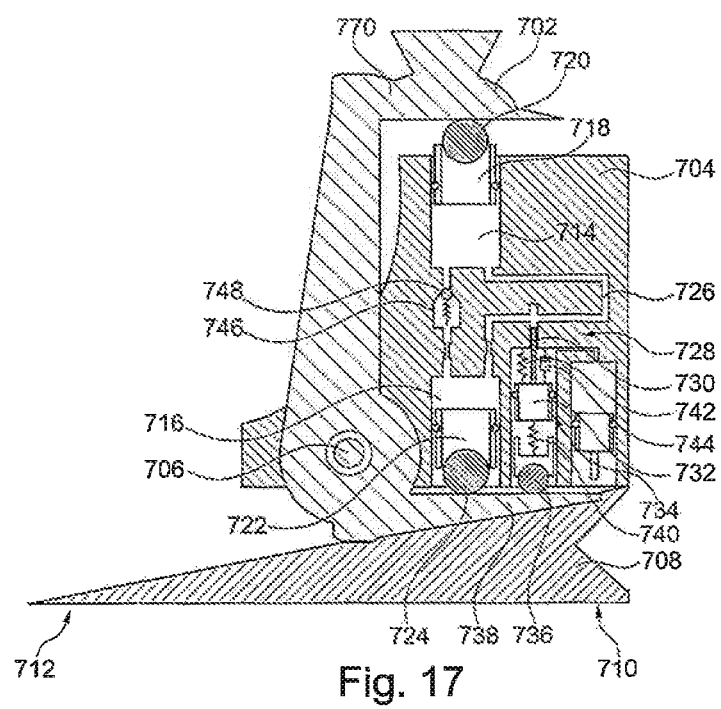
FIG. 17 is a diagrammatical illustration of a joint according to an embodiment of this invention.
Figure 18:
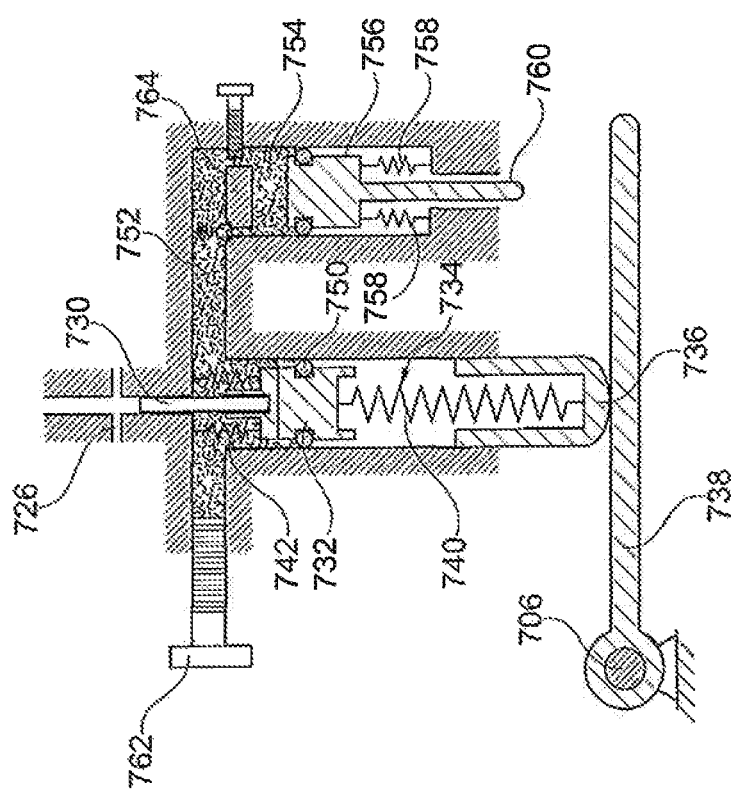
FIGS. 18 to 21 show diagrammatical illustrations of the non-electrical mechanism in different stages during "walking" and FIGS. 22 to 24 show the non-electrical mechanism from FIGS. 18 to 21 in different stages during "standing".

FIG. 17 shows a prosthetic foot with an ankle joint pursuant to an embodiment of this invention. The first connector 702 and the second connector 704 are connected to each other pivoting via a joint 706. An only diagrammatically illustrated prosthesis foot 708 is also placed on the second connector 704. It has a heel area 710 and a toe area 712 which can also be called forefoot or forefoot area.

In the second connector 704, there is the first chamber 714 and the second chamber 716. In these, there is the first piston 718, on which there is a first cam plunger 720 and a second piston 722 with a second cam plunger 724. A cam plunger can also be called a follower.

The two chambers 714, 716 are connected to each other via a fluid connection 726.

The fluid connection 26 can be occluded by means of a closure 728. This has a pin 730, which is placed on a carrier element 732.

The carrier element 732 is placed in a hollow 734 in which there is a third cam plunger 736 in the lower part in FIG. 17. It abuts to the lower cam 738, which is part of the first connector 702. If the first connector 702 is now pivoted relative to the second connector 704 so that the lower cam 738 is moved up, the third cam plunger 736 is moved up, which compresses the spring 740 and exerts a force upwards onto the carrier element 732. Above the carrier element 732, there is another spring 742 and a dampening element 744 that ensures that the carrier element 732 and the pin 730 aligned on it are moved up with a time delay. The individual phases of a gait cycle and the standing phase are explained in more detail in the further FIGURES.

Between the first chamber 714 and the second chamber 716, there is a one-way connection 746, in which a check valve 748 is placed.

FIGS. 18 to 24 show an enlarged section of the device shown in FIG. 17 in different states. Each shows the lower cam 738 in different positions and the third cam plunger 736. FIG. 18 once again serves the precise designation of the different construction elements. The lower cam 738 is borne pivoting around the joint 706 and abuts to the third cam plunger 736. Between it and the carrier element 732, there is the spring 740 in the hollow 734. The upper part of this hollow is separated from the lower part in which the spring 740 is located by a sealing ring 750. This upper part is filled with a fluid that can flow through a fluid connection 752 into a dampening chamber 754 that is closed off to the bottom by a dampening piston 756. At its end, further springs 758 and a thrust rod 760 are placed.

The volume of the dampening chamber 754 and the upper part of the hollow 734 can be set by a volume adjustment screw 762. A flow rate 764 between the connection 752 and the dampening chamber 754 can be set by a throttle screw 766. It can be appreciated that, in contrast to FIG. 17, the dampening element 744 has been removed since it is now formed by the dampening chamber 754 and the dampening piston 756 with the springs 758. The pin 730 can further be moved upwards to close the fluid connection 726.

Figure 19:
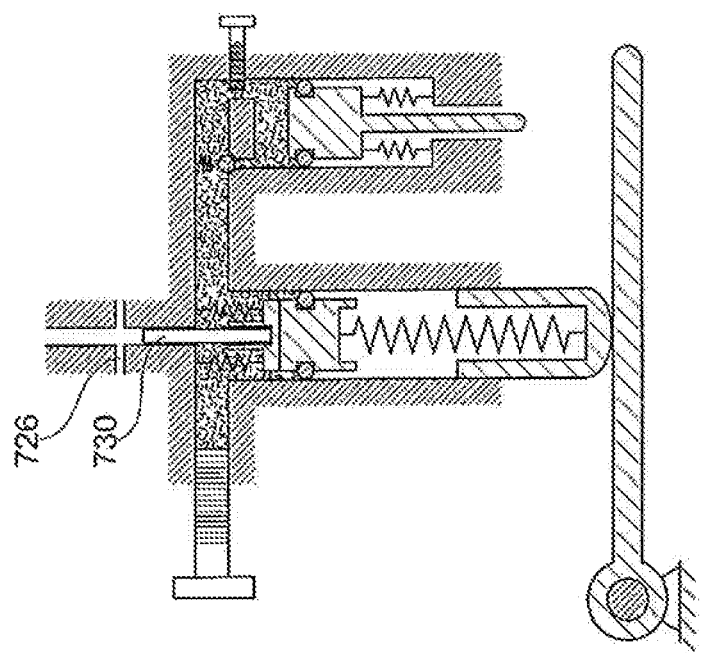
Figure 20:
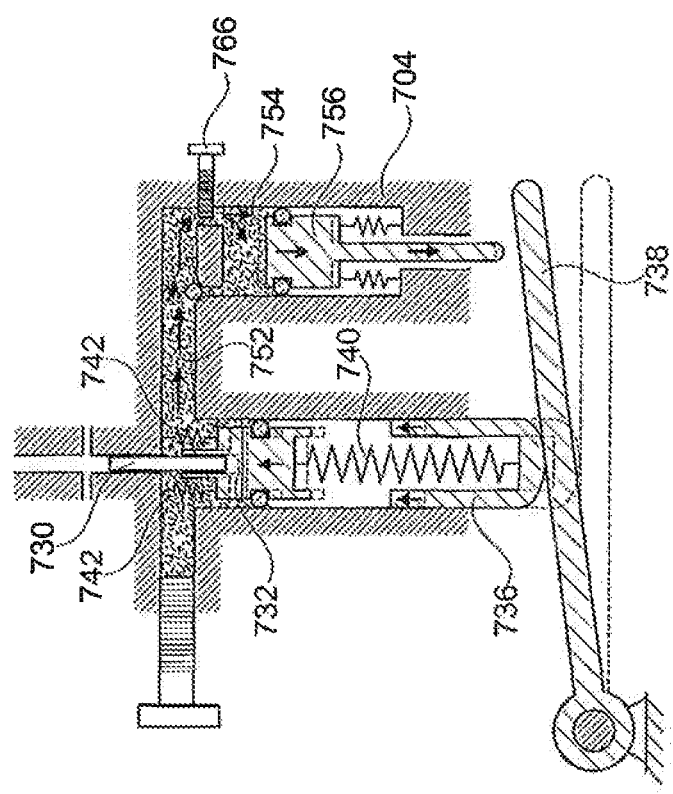
Figure 21:
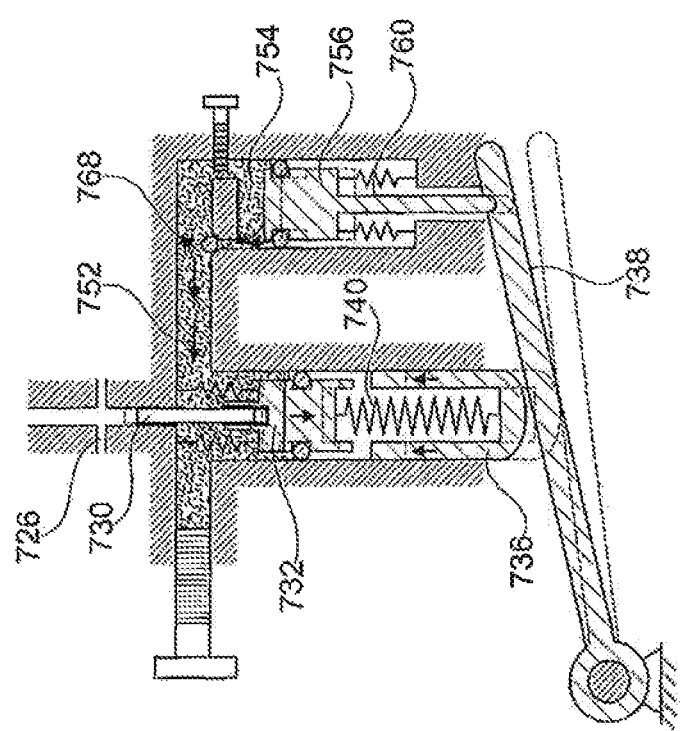

FIGS. 19 to 21 show the situations in different phases of the gait cycle. FIG. 19 shows the situation right after putting down the foot at approx. 10° plantarflexion. The pin 730 has not closed the fluid connection 726, so that fluid from the first chamber 714 can flow into the second chamber 716 and vice versa.

FIG. 20 shows the middle standing phase. It can be appreciated that the lower cam 738 has been pivoted relative to the second connector 704. Thus, an upward force has been applied to the third cam plunger 736, upon which it has moved from the position illustrated in a dashed line to the new position. Thus, the spring 740 is compressed and pushes the carrier element 732 upwards against the springs 742. At the same time, fluid is routed through the fluid connection 752 past the throttle screw 766 into the dampening chamber 754, which pushes the dampening piston 756 down. The resulting dampening leads to a time delay between the movement of the third cam plunger 736 and the carrier element 732 with the pin 730 on it.

FIG. 21 shows the situation in dorsiflexion. The lower cam 738 has been pivoted further, so that the third cam plunger 736 continues to be subject to an upwards force, moving it upwards and further compressing the spring 740. In this strong deflection, the thrust rod 760 is also applied to the lower cam 738 and is also pushed up by its movement. Thus, the dampening piston 756 is also pushed up, and thus moves the fluid in the dampening chamber 754 past the backpressure valve 768 and through the fluid connection 752. Thus, a pressure is applied on the carrier element 732 from above, because of which it moves downwards against the pressure of the spring 740 and thus also moves down the pin 730. Therefore, the pin 730 cannot close the fluid connection 726 during a step.

Figure 22:
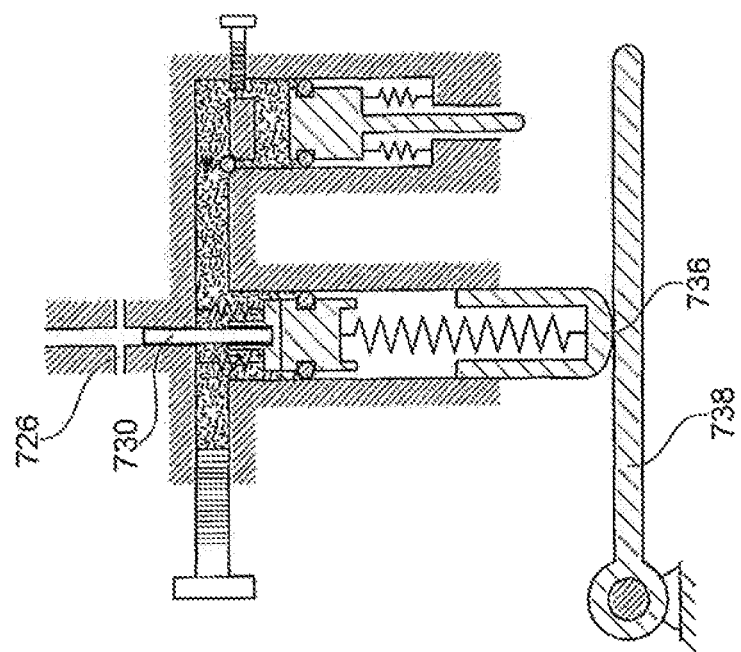

This is different when standing. FIG. 22 corresponds to FIG. 19 and shows the situation at approximately 10° plantarflexion. The pin 730 does not close the fluid connection 726. The lower cam 738 is in contact with the third cam plunger 736.

Figure 23:
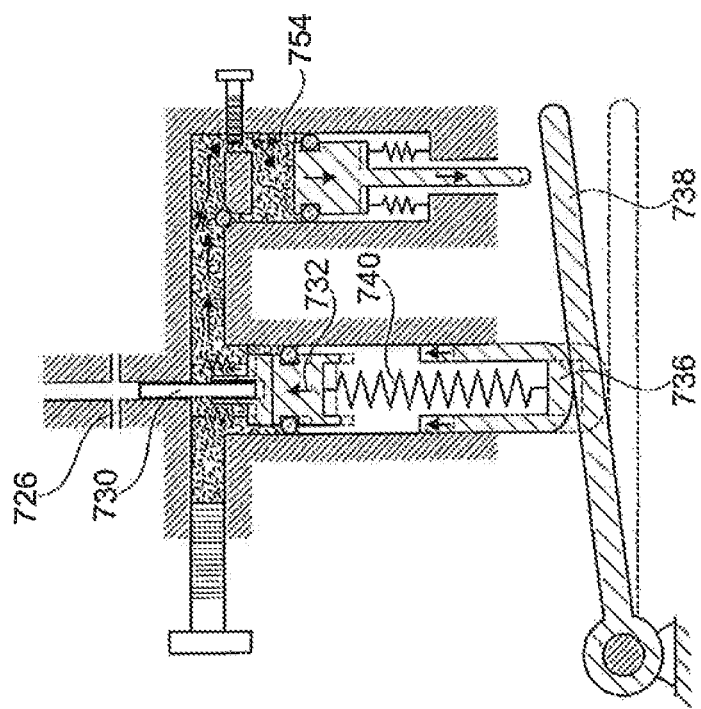

FIG. 23 corresponds to FIG. 20 and shows how the pivoting of the lower cam 738 moves the third cam plunger 736 upwards and thus pushes fluid into the dampening chamber 754 via the spring 740 around the carrier element 732. At the same time, the pin 730 is pushed up, but does not close the fluid connection 726 yet.

Figure 24:
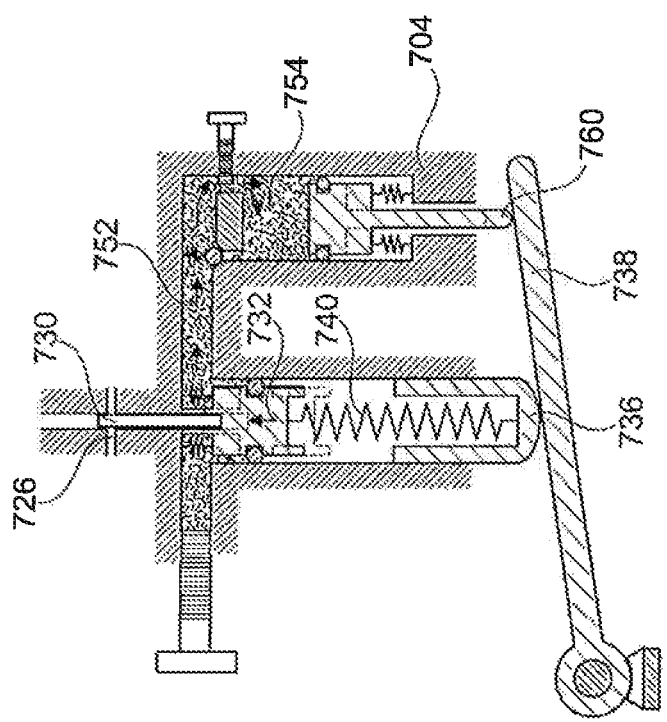

Since the wearer of the prosthesis remains in this state, the spring 740 can relax further. This is shown in FIG. 24, the lower cam 738 has not moved relative to the second connector 704 and thus also to the third cam plunger 736. By relieving the spring 740, however, the carrier element 732 is moved up and pushes further fluid through the fluid connection 752 into the dampening chamber 754. The thrust rod 760 is not yet in contact with the lower cam 738.

The pin 730 was moved in this situation so that it closes the fluid connection 726, so that, as shown in FIG. 17, no further fluid can flow from the second chamber 716 into the first chamber 714. Further movement of the foot in the direction of a dorsiflexion thus is not possible.

To release this lock and this closure and to put the ankle joint from the mode "standing" to the mode "walking", the wearer of the prosthesis must apply a clockwise torque on the first connector 702 or a counterclockwise torque on the second connector 704 in the embodiment shown. This moves the upper cam 770 down and pushes the first piston 718 down via the first cam plunger 720, so that the volume of the first chamber 714 is reduced. Fluid enters the second chamber 716 through the backpressure valve 748 without having to pass the fluid connection 726. The pivoting of the first connector 702 relative to the second connector 704, which corresponds to a pivoting of the lower cam 738 downwards in FIG. 18, permits springs 740 and 742 to relieve, which moves the carrier element 732 and the pin 730 down, so that the fluid connection 726 is released again.

The invention claimed is:

1. A prosthetic joint, comprising:
   a first connector, a second connector, and a pivot device that allows the first and second connectors to rotate with respect to each other;
   a first chamber and a second chamber, wherein the first and second chambers are connected via a bi-directional flow path;
   a valve positioned in the bi-directional flow path and configured to restrict fluid flow between the first and second chambers; and
   a non-electronic mechanism for controlling the fluid flow responsive to a rate of change of position of the joint,
   wherein an external force applied to the prosthetic joint causes the valve to open and to permit fluid flow between the first and second chambers, wherein the external force may be applied to the prosthetic joint by transferring weight to a heel of the user.

2. The prosthetic joint of claim 1, wherein the valve comprises a one-way valve.

3. The prosthetic joint of claim 1, wherein the mechanism is arranged such that a dwell at a particular joint location or locations will close the valve.

4. The prosthetic joint of claim 1, further comprising an occlusion configured to restrict fluid flow between the first and second chambers within the bi-directional flow path.

5. The prosthetic joint of claim 4, wherein the occlusion is connected to a damping element that opposes movement of the occlusion when the occlusion moves to restrict fluid flow between the first and second chambers within the bi-directional flow path.

6. The prosthetic joint of claim 1, further comprising a uni-directional flow path connecting the first chamber and the second chamber.

7. A prosthetic joint, comprising:
   a first connector, a second connector, and a pivot device that allows the first and second connectors to rotate with respect to each other;
   a first chamber and a second chamber, wherein the first and second chambers are connected via a bi-directional flow path;
   a valve positioned in the bi-directional flow path and configured to restrict fluid flow between the first and second chambers;
   a non-electronic mechanism for controlling the fluid flow responsive to a rate of change of position of the joint,
   wherein an external force applied to the prosthetic joint causes the valve to open and to permit fluid flow between the first and second chambers; and
   an occlusion configured to restrict fluid flow between the first and second chambers within the bi-directional flow path, wherein the occlusion is connected to a damping element that opposes movement of the occlusion when the occlusion moves to restrict fluid flow between the first and second chambers within the bi-directional flow path, wherein the joint further comprises a cam driving a follower; and wherein the follower position drives closure of the occlusion through a compliant element.

8. The prosthetic joint of claim 7, wherein the cam and occlusion are configured to occlude the bi-directional flow path between the first and second chambers when the joint is stopped, nearly stopped, and/or at a particular angular location for a period of time defined by the mechanism dynamics.

9. The prosthetic joint of claim 8, wherein the valve is configured to permit fluid flow within the bi-directional flow path between the first and second chambers when the valve is opened by the external force applied to the prosthetic joint.

10. The prosthetic joint of claim 9, wherein opening the valve is configured to remove the occlusion from the bi-directional flow path and to permit fluid flow within the bi-directional flow path between the first and second chambers.

11. A prosthetic joint, comprising:
    a first connector, a second connector, and a pivot device that allows the first and second connectors to rotate with respect to each other;
    a first chamber and a second chamber, wherein the first and second chambers are connected via a bi-directional flow path and a one-way connection;
    an occlusion positioned in the bi-directional flow path and configured to restrict fluid flow between the first and second chambers;
    a valve positioned in the one-way connection and configured to restrict fluid flow between the first and second chambers; and
    a non-electronic mechanism for controlling the fluid flow responsive to a rate of change of position of the joint,
    wherein a first external force applied to the prosthetic joint causes the valve to open and to permit fluid flow between the first and second chambers, wherein the first external force may be applied to the prosthetic joint by transferring weight to a heel of the user.

12. The prosthetic joint of claim 11, wherein the valve comprises a one-way valve.

13. The prosthetic joint of claim 11, wherein the first external force may be a torque applied to the first connector.

14. The prosthetic joint of claim 11, wherein the first external force may be a torque applied to the second connector.

15. The prosthetic joint of claim 14, wherein a second external force applied to the prosthetic joint results in application of a damping force on the occlusion to insert the occlusion into the bi-directional flow path to restrict fluid flow between the first and second chambers.

16. The prosthetic joint of claim 15, further comprising a hollow and a cam plunger positioned within the hollow, wherein the occlusion is attached to the cam plunger.

17. The prosthetic joint of claim 16, wherein the first connector comprises a lower cam and rotation of the lower cam in a first direction pushes up the cam plunger and inserts the occlusion into the bi-directional flow path to restrict fluid flow between the first and second chambers.

18. The prosthetic joint of claim 17, wherein rotation of the lower cam in a second direction pulls the cam plunger and removes the occlusion out of the bi-directional flow path to permit fluid flow between the first and second chambers.

19. The prosthetic joint of claim 11, wherein the occlusion comprises a pin.

* * * * *